US006929631B1

(12) United States Patent
Brugger et al.

(10) Patent No.: US 6,929,631 B1
(45) Date of Patent: Aug. 16, 2005

(54) METHOD AND APPARATUS FOR PERCUTANEOUSLY ACCESSING A PRESSURE ACTIVATED IMPLANTED PORT

(75) Inventors: James M. Brugger, Newburyport, MA (US); Jeffrey H. Burbank, Boxford, MA (US); Charles D. Finch, Jr., Clinton, MS (US); Hendrik K. Kuiper, Edwards, MS (US)

(73) Assignee: VAScA, Inc., Tewksbury, MA (US)

( * ) Notice: Subject to any disclaimer, the term of this patent is extended or adjusted under 35 U.S.C. 154(b) by 0 days.

(21) Appl. No.: 09/595,167

(22) Filed: Jun. 15, 2000

Related U.S. Application Data

(60) Continuation-in-part of application No. 09/239,411, filed on Jan. 28, 1999, now abandoned, and a continuation-in-part of application No. 09/561,374, filed on Apr. 28, 2000, now abandoned, which is a continuation of application No. 09/017,045, filed on Feb. 2, 1998, now Pat. No. 6,056,717, which is a continuation of application No. 08/745,903, filed on Nov. 7, 1996, now Pat. No. 5,755,780, which is a continuation of application No. 08/480,117, filed on Jun. 7, 1995, now abandoned, which is a division of application No. 08/183,151, filed on Jan. 18, 1994, now Pat. No. 5,562,617, which is a continuation of application No. 08/634,634, filed on Apr. 18, 1996, now Pat. No. 5,713,859, which is a continuation of application No. 08/183,151, filed on Jan. 18, 1994, now Pat. No. 5,562,617.

(51) Int. Cl.[7] .............................................. A61M 31/00
(52) U.S. Cl. ...................... 604/502; 604/891; 604/247; 604/288.01; 604/228.04; 604/93.01
(58) Field of Search ........................... 604/30, 500, 502, 604/236, 890.1, 167.01–167.04, 164.02, 604/246, 256, 288.01, 288.03, 288.04, 537, 604/175, 244, 131, 151, 124, 125, 93.01, 604/8–10

(56) References Cited

U.S. PATENT DOCUMENTS

| 4,181,132 | A | | 1/1980 | Parks |
| 4,464,178 | A | | 8/1984 | Dalton |
| 4,534,759 | A | * | 8/1985 | Trawoger ..................... 251/354 |
| 4,544,371 | A | * | 10/1985 | Dormandy et al. .......... 604/185 |
| 4,569,675 | A | * | 2/1986 | Prosl et al. .......... 128/DIG. 26 |
| 4,639,247 | A | * | 1/1987 | Bokros ....................... 604/175 |
| 4,681,560 | A | * | 7/1987 | Schulte et al. ................. 604/9 |
| 4,705,501 | A | * | 11/1987 | Wigness et al. ............ 604/175 |
| 4,846,806 | A | * | 7/1989 | Wigness et al. ............ 604/175 |
| 4,850,955 | A | * | 7/1989 | Newkirk ........................ 604/9 |

(Continued)

FOREIGN PATENT DOCUMENTS

WO  WO 93/00129 A1  1/1993

(Continued)

*Primary Examiner*—Cris L. Rodriguez
(74) *Attorney, Agent, or Firm*—Townsend and Townsend and Crew LLP

(57) ABSTRACT

Methods and apparatus for percutaneously accessing an implanted port using an access tube which is periodically introduced to the implanted port. The apparatus is preferably an implantable port having a pressure-responsive valve element. It has been found that repeated passage of the access tube through the same tissue tract to the implantable port reduces patient trauma, with minimized bleeding and reduction in sensitivity. The tract may be initially formed by percutaneously placing a penetrating element through intact skin to the port and leaving the element in place for a time sufficient to created the tract.

7 Claims, 8 Drawing Sheets

U.S. PATENT DOCUMENTS

| | | |
|---|---|---|
| 4,892,518 A | 1/1990 | Cupp et al. |
| 5,053,013 A | 10/1991 | Ensminger et al. |
| 5,057,084 A | 10/1991 | Ensminger et al. |
| 5,098,405 A | 3/1992 | Peterson et al. |
| 5,125,897 A | 6/1992 | Quinn et al. |
| 5,180,365 A | 1/1993 | Ensminger et al. |
| 5,190,525 A | 3/1993 | Oswald et al. |
| 5,226,879 A | 7/1993 | Ensminger et al. |
| 5,257,971 A * | 11/1993 | Lord et al. .................. 604/153 |
| 5,263,930 A | 11/1993 | Ensminger |
| 5,281,199 A | 1/1994 | Ensminger et al. |
| 5,290,263 A * | 3/1994 | Wigness et al. ............ 604/247 |
| 5,306,255 A | 4/1994 | Haindl |
| 5,350,360 A | 9/1994 | Ensminger et al. |
| 5,417,656 A | 5/1995 | Ensminger et al. |
| 5,476,451 A | 12/1995 | Ensminger et al. |
| 5,503,630 A | 4/1996 | Ensminger et al. |
| 5,520,643 A | 5/1996 | Ensminger et al. |
| 5,527,277 A | 6/1996 | Ensminger et al. |
| 5,527,278 A | 6/1996 | Ensminger et al. |
| 5,562,617 A | 10/1996 | Finch, Jr. et al. |
| 5,702,363 A | 12/1997 | Flaherty |
| 5,713,859 A | 2/1998 | Finch, Jr. et al. |
| 5,741,228 A | 4/1998 | Lambrecht et al. |
| 5,897,528 A | 4/1999 | Schultz |
| 5,989,239 A | 11/1999 | Finch et al. |
| 6,162,238 A * | 12/2000 | Kaplan et al. .................. 604/9 |
| 6,206,871 B1 * | 3/2001 | Zanon et al. ................ 604/131 |
| 6,299,609 B1 * | 10/2001 | Finch et al. ................. 604/502 |
| 6,478,783 B1 * | 11/2002 | Moorehead ............ 604/288.02 |
| 6,544,214 B1 * | 4/2003 | Utterberg ................. 604/93.01 |

FOREIGN PATENT DOCUMENTS

| | | |
|---|---|---|
| WO | WO 95/19200 | 7/1995 |
| WO | WO 96/31246 | 10/1996 |
| WO | WO 97/47338 | 12/1997 |

\* cited by examiner

METHOD AND APPARATUS FOR PERCUTANEOUSLY ACCESSING A PRESSURE ACTIVATED IMPLANTED PORT

CROSS-REFERENCES TO RELATED APPLICATIONS

This application is a Continuation-In-Part of U.S. patent application Ser. No. 09/239,411 filed Jan. 28, 1999, now abandoned and also is a Continuation-In-Part of U.S. patent application Ser. No. 09/561,374, filed Apr. 28, 2000, now abandoned which was a Continuation of application Ser. No. 09/017,045, filed Feb. 2, 1998, now U.S. Pat. No. 6,056,717, which was a Continuation of application Ser. No. 08/745,903, filed Nov. 7, 1996, now U.S. Pat. No. 5,755,780, which was a Continuation of application Ser. No. 08/480,117, filed Jun. 7, 1995, now abandoned, which was a Division of application Ser. No. 08/183,151, filed Jan. 18, 1994, now U.S. Pat. No. 5,562,617, and which also was a Continuation of application Ser. No. 08/634,634, filed Apr. 18, 1996, now U.S. Pat. No. 5,713,859, which was a Continuation of application Ser. No. 08/183,151, filed Jan. 18, 1994, now U.S. Pat. No. 5,562,617, all of which are incorporated herein by reference.

BACKGROUND OF THE INVENTION

1. Field of the Invention

The present invention relates generally to the design and use of medical devices, and more particularly to the design and use of an implantable port having a simplified design that establishes temporary access to a body lumen in the patient.

Access to a patient's vascular system can be established by a variety of temporary and permanently implanted devices. Most simply, temporary access can be provided by the direct percutaneous introduction of a needle through the patient's skin and into a blood vessel. While such a direct approach is relatively simple and suitable for some applications, they are not suitable for hemodialysis, peritoneal dialysis, and hemofiltration. Such a direct approach is also inconvenient for other procedures, such as insulin or drug delivery procedures, which are repeated frequently over the lifetime of the patient.

A variety of implantable ports have been proposed over the years to provide long-term vascular access for hemodialysis, hemofiltration, and other medical treatments. Typically, the port includes a chamber having an access region, such as a septum, where the chamber is attached to an implanted cannula which in turn is secured to a blood vessel. In the case of veins, the cannula is typically indwelling, and in the case of arteries, the cannula may be attached by conventional surgical technique. Percutaneous access to a port through a septum is generally limited to small diameter, non-coring needles. Large diameter needles will core the septum, i.e. form permanent channels therethrough, which will destroy the septum after repeated uses. Unfortunately, even the use of small diameter, non-coring needles will eventually cause a septum to fail due to repeated septum penetrations.

Implantable ports having an access aperture and internal valve mechanism for isolating the implanted cannula have also been proposed. One type of implantable valved port is described in a series of issued of U.S. patents which name William Ensminger as inventor. The Ensminger access ports have internal lumens for receiving a percutaneously introduced needle and an internal valve structure for isolating the port from an associated implanted cannula. Generally, the Ensminger ports have a needle-receiving aperture which is oriented at an inclined angle relative to the patient's skin. The Ensminger ports employ relatively entry ports having large funnel-like tapers and troughs so that needles can be introduced through many different sites in accordance with conventional procedures. The Ensminger patents do not describe port access using large diameter, coring needles, such as fistula needles. Moreover, as many of the specific Ensminger designs employ elastomeric valve elements, it is likely that the valve mechanisms would be damaged if the ports were accessed by a fistula needle or other large bore coring needle. Representative Ensminger patents are listed in the Description of the Background Art below.

Although promising, these known valve-type implantable ports are not without limitations. For one thing, these known ports are expensive and that limits their applicability to a broader range of medical treatments. Such implantable ports typically have an interior structure having many moving parts and elements as evidenced by the devices of the Ensminger patents. The complicated interior of these known ports increases the cost per part of each implantable port. Although not true in all circumstances, the additional parts may also increase the probability that one of these parts may fail. The plurality of parts also increases the level of skill required to assemble each implantable port. Additionally, some of these known implantable ports still have valves which contact the needle and will wear out due to needle damage incurred during repeated use. Furthermore, to the extent that implantable ports have been used, it has generally been recommended that the access site be moved relative to the port in order to change the location of the tissue tract between successive access procedures.

For these reasons, it would be desirable to provide improved methods and apparatus for percutaneously accessing a patient's vasculature. The improved methods and apparatus should reduce patient trauma, reduce cost, simplify apparatus design, provide for reliable access to the vasculature, minimize the risk of infection to the patient, and preferably require only minor modifications to present procedures. At least some of these objectives will be met by the invention described hereinafter.

2. Description of the Background Art

U.S. Pat. No. 5,562,617 and WO 95/19200, assigned to the assignee of the present application, describe implantable vascular access systems comprising an access port having an internal slit or duck bill valve for preventing back flow into the port. Vascular access ports having various articulating valves for isolating the port from the vascular system in the absence of external percutaneous connection to the port are described in the following U.S. patents which name William Ensminger as an inventor: U.S. Pat. Nos. 5,527,278; 5,527,277; 5,520,643; 5,503,630; 5,476,451; 5,417,656; 5,350,360; 5,281,199; 5,263,930; 5,226,879; 5,180,365; 5,057,084; and 5,053,013. Other patents and published applications which show implantable ports having valve structures opened by insertion of a needle include U.S. Pat. Nos. 5,741,228; 5,702,363; 4,569,675; 4,534,759; 4,181,132; WO 97/47338; and WO 96/31246. Devices for hemodialysis or devices having one piece valves are described in U.S. Pat. Nos. 4,892,518; 5,098,405; and 5,125,897. Implantable ports and subcutaneous catheters for connecting the ports for hemodialysis, peritoneal dialysis, and other procedures which may be useful in the present invention are described in co-pending application Ser. Nos. 08/539,105; 08/724,948; 09/009,758; 08/942,990; 08/857,386; 08/896, 791; 08/856,641; and 09/003,772, the full disclosures of which are incorporated herein by reference.

SUMMARY OF THE INVENTION

The present invention provides improved methods, apparatus, and kits for creating and establishing access to subcutaneously implanted ports for a variety of medical purposes such as drug delivery and the like. The present invention advantageously provides implantable ports of a simplified design and construction which open and close based on various levels of pressure differentials.

In particular, the present invention preferably provides methods and apparatus which combine the advantages of a "buttonhole" access technique, such as low pain needle insertion and formation of a denervated tissue tract, with the advantages of subcutaneous port access, e.g. reliable performance and low failure rates, high blood and fluid flows through the port with minimum degradation of the blood or other fluid, and the ability to utilize an internal valve to provide improved isolation of the blood vessel or other accessed body lumen. Such a buttonhole access technique is described in commonly assigned, co-pending U.S. patent application Ser. No. 09/161,068, (filed on Sep. 25, 1998), the full disclosure of which is incorporated herein by reference for all purposes. It has been observed that the tissue tracts created and utilized by the present invention are not the same type of tunnel which is developed over time with "button hole" fistula access technique known in the art. It is presently believed that the improved tissue tract formed by the present invention results at least partly from the ability of a valved or other self-closing port to inhibit back bleeding into the tissue tract when the needle is withdrawn. The inhibition of back bleeding substantially eliminates the need to remove blood clots from the track (which is painful for the patient) and thus reduces the risk of blood clot embolism.

In a first aspect of the present invention, an implantable port for use in medical procedures comprises a body having a flow passage therethrough. The flow passage has an upstream end and a downstream end, where at least one portion of the upstream end is adapted to sealingly engage an access tube that is inserted into said upstream end. This passage is optionally tapered so as to facilitate the sealing engagement with the access tube. The taper in the passage can also advantageously accommodate needles of slightly varying diameters. A pressure-responsive valve element is positioned in the flow passage downstream from the upstream portion so that the access tube can be fully inserted into said upstream portion without engaging the valve element. The pressure-responsive valve element is preferably closed in the absence of a differential pressure above a threshold level.

In one embodiment, the port according to the present invention has a body comprising a housing and a housing insert. The housing may be made of a noncorrosive material such as stainless steel or titanium while the insert is typically made of a compliant material such as silicone. In other embodiments, the housing and housing insert may made from the same homogenous material. The implantable port design is preferably simplified by having the pressure-responsive valve element integrally formed with the insert. In this manner, the interior structure of the port may be simplified for cost-effective manufacturing. Use of such an integrated pressure valve element is possible in the port since not all medical applications may require the bidirectional flow capability used for such extracorporal procedures as hemodialysis and the like. Although such bidirectional flow may still be possible if sufficient suction or differential pressure is present, the pressure-responsive valve of the present embodiment is particularly suited for fluid infusion such as for drug delivery. The threshold level of pressure required to activate the valve is preferably about 2 psi.

The port according to the present invention generally has an opening on the upstream end of the passageway with dimensions which correspond to those of the access tube, e.g. they will have similar diameters, or with an opening comprising a funnel having dimensions substantially larger than the access tube diameter. Usually, however, provision of such a funnel at the opening for directing the access tube into the opening is undesirable since it allows the user to penetrate the access tube through different access tracts. To minimize wear and needle damage after the penetration into the port, the downstream end of the passageway in the port body is preferably disposed at a 90° angle relative to the upstream end which receives the access tube. Of course, the passageway may be disposed at other angles in the passageway. The bend in the passageway prevents the access tube from contacting and damage the pressure-responsive valve element.

According to a second aspect of the present invention, a method for delivering a substance to a subcutaneous target site comprises percutaneously introducing an access tube to an implanted port having a flow passageway with an upstream end, a downstream end, and a valve element therein. The access tube is introduced to seat in the passage but the tube does not engage the valve element. The access tube and a seat interface in the passages form a seal. This minimizes needle damage to a fluid path sealing element of the port, something that plagues the performance of conventional ports.

The substance is introduced into the flow passage through the access tube at a pressure sufficient to open the valve element to permit flow through the flow passageway to the target site. Over time, repeated percutaneous introductions of the access tube into the patient will create a unique tissue tract which becomes lined with scar tissue and has lessened nerve sensitivity, reducing patient trauma as the same tissue tract continues to be used for access. In some cases, after the access tract is established, it will not be necessary to provide a sharpened element in order to assist in percutaneous introduction. That is, a blunt cannula may be able to pass inwardly through the established tissue tract. Usually, the access tube will have a diameter which is larger than that of the tissue tract which will have collapsed after the cannula was removed in the previous treatment protocol. Thus, as the blunt cannula is introduced through the established tissue tract, the tissue tract will be dilated.

Usually, the access intervals and time periods will depend at least in part on the procedures to be performed on the patient. For example, patients undergoing insulin treatments will typically have the needle or cannula introducing step repeated at intervals of up to four times a day, usually for indefinite periods. Usually, although not necessarily, the needle or cannula will be introduced in a consistent direction, e.g. generally normal or perpendicular to the skin surface through which it is being introduced, with the repeated access steps eventually creating the nerve depleted tissue tract described above. By introducing the needle or cannula normal to the skin surface, the tissue tract may be formed vertically, thus lessening its length and further reducing bleeding and patient trauma. The access port is also particularly easy to locate beneath the skin, and when combined with the ability to vertically introduce the needle, targeting of the port is greatly simplified. The ability to accurately and simply target the port lessens the chance that the cannula will be misdirected, still further reducing patient trauma and enhancing the unique tissue tract formation which underlies the present invention.

Kits according the present invention may comprise an implantable port together with instructions for use setting forth any of the methods described for implanting the port and creating a cannula access tract to the port. The port and the instructions for use will typically be packaged together, using any of the packages described hereinafter, and other kit components, such as a penetrating element, access tube, or the like, may also be provided.

A further understanding of the nature and advantages of the invention will become apparent by reference to the remaining portions of the specification and drawings.

DESCRIPTION OF THE SPECIFIC EMBODIMENTS

The methods and apparatus of the present invention for percutaneously accessing an implantable port is useful in a variety of long-term medical procedures such as insulin drug delivery and the like. The methods of the present invention may be performed with implantable ports having one, two, three, or more, discrete access ports which may be vertically or otherwise repeatedly aligned with the access tract to be percutaneously formed through overlying tissue. Such access tracts will be useful for repeated access to the aperture, where the aperture defines a specific target site through the overlying tissue. The use of valved ports provide for positive shutoff and isolation of the attached body lumen, and in particular provide for complete cessation of back bleeding when an access tube is removed from ports attached to blood vessels. An implantable port of the present design advantageously allows for frequent cannulation without a septum to wear out. Additionally, the use of an implantable port with the buttonhole tissue tract facilitates frequent drug delivery injections and thus promotes better compliance to drug insulin therapy in a diabetic patient.

The preferred implantable ports will have at least one opening or aperture which removably receives the access tube, optionally in a vertical orientation in order to minimize distance of the tissue tract. The implantable port will preferably be capable of immobilizing the access needle while fluid is being transferred through the port. Typically, the port will be implanted beneath the skin by a distance in the range from about 3 mm to 20 mm, usually from 5 mm to 15 mm. In preferred embodiments, the access needle N comprises or is coupled to a pressure source that can be used to open a pressure-responsive valve. Such a valve is generally responsive to pressure differentials created by a pressure source such as a syringe. In some embodiments, however, the valve may be a bidirectional if a suction source or sufficient pressure differential is present to activate the valve for injection and extraction.

Figure 1:
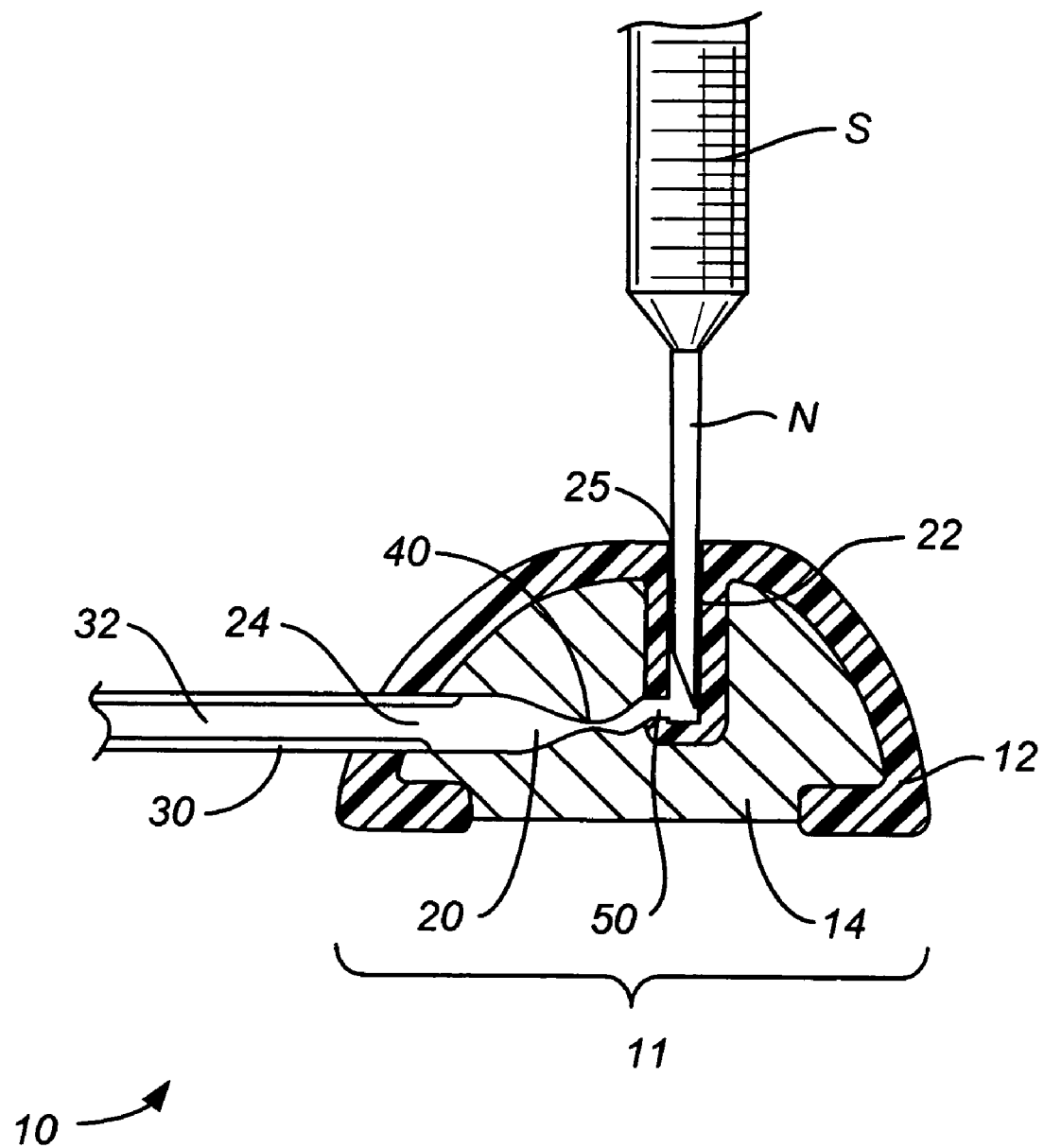
FIG. 1 is a cross-sectional view of a first embodiment of an implantable port according to the present invention.

Referring now to FIG. 1, an implantable port 10 having a body 11 in accordance with the principles of the present invention will be described. In the embodiment shown in FIG. 1, implantable port 10 comprises the body 11 having a housing 12 optionally made of a non-corrosive material such as stainless steel or titanium and a housing insert 14 optionally made of a compliant material such as silicone or other elastomeric material. The body 11 defines a flow passage 20 having an upstream end 22 adapted to sealingly engage an access tube N inserted into the upstream end of the passage 20. The passage 20 preferably has an opening or aperture 25 located on an upper surface of the body 11. In one embodiment, such a seal may be formed in the upstream end 22 by having the end 22 formed as a tapered passage so that the side walls of an access tube such as a needle or cannula radially engages the passage. The upstream end 22 of the passage 20 may be tapered to fit with a variety of different sized needles. Optionally, the passage 20 may use other sealing devices in end 22 such as an elastomeric ring or tube to form a radial seal with the needle N. The needle N may also comprise a non-standard needle having a beveled distal tip to facilitate the radial engagement with the passage 20 or an elastomeric O-ring. A conventional needle may damage the O-ring during insertion.

Figure 2:
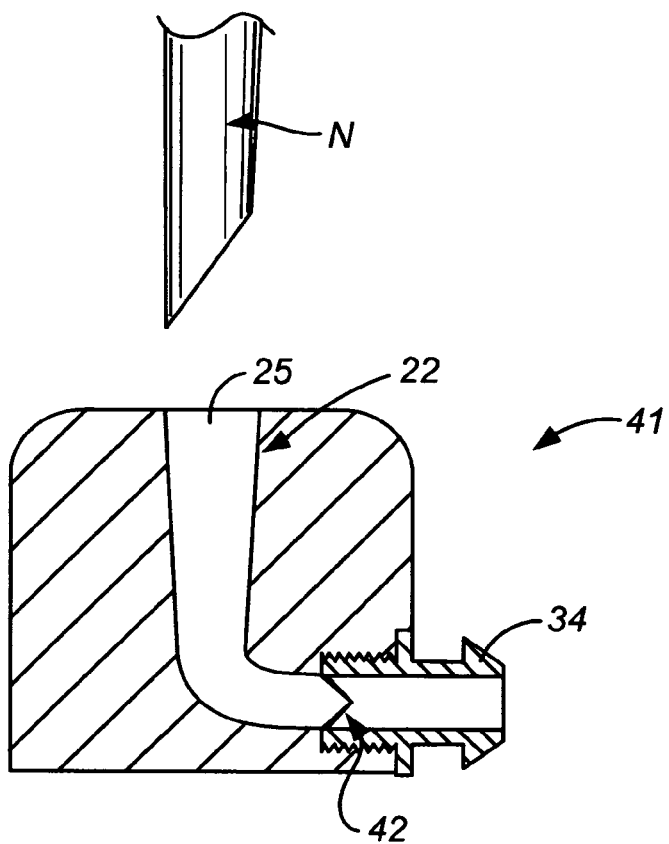
FIGS. 2–3 are cross-sectional views of another embodiment of an implantable port according to the present invention being accessed by an access tube.
Figure 3:
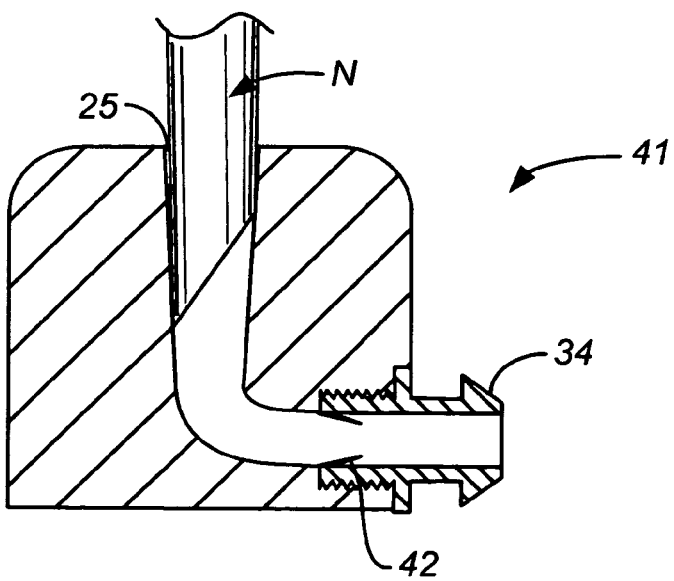

As shown in FIG. 1, a catheter 30 with a lumen 32 or similar elongate tubing is connected to the passage 20 near the downstream end 24 to deliver fluids or materials injected by the needle N to a target site within the body. FIGS. 2 and 3 also illustrate an outlet or nipple 34 which may be used to releasably couple the implantable port 10 with catheter 30. For insulin drug delivery, the catheter 30 is substantially similar to standard catheters used with insulin pumps known in the art.

Referring now to FIGS. 1–3, a pressure-responsive valve element 40 is positioned in the flow passage 20 downstream from the upstream end or portion 22 of the passage. In the embodiment of FIG. 1, the pressure-responsive valve element 40 is a pressure-actuated slit valve that is optionally integrally formed in the housing insert 14 to define an integrally formed component. In other embodiments as shown in FIGS. 2–3, the pressure-responsive valve element 40 may be a separate element such as an articulating leaflet valve, preferably allowing flow in only one direction. Sufficient pressure differential, however, may still allow bidirectional flow if slit valves are used. Preferably, the pressure-responsive valve element 40 is positioned in the flow passage 20 such that the access tube or needle N can be fully inserted into the upstream portion 22 without engaging the valve element. The valve element 40 typically remains in a closed state in the absence of a differential pressure above a threshold level. For example, for syringe drug delivery such as insulin injections, the valve element will open when pressure exceeds a threshold level of about 0.25 to 25.0 psi, preferably about 1–5 psi.

As shown in the embodiments of FIGS. 2–3, pressure responsive valve element is not necessarily integrally formed with the insert 14 of the implantable port 10. In some embodiments, the body of implantable port 41 is made of a homogenous material and the valve element such as articulating valve 42 is attached to this homogenous material. Additionally, as seen in FIG. 2, a valve such as the articulating valve 42 may be incorporated into part of the nipple element 34 which is screwed or threaded into the port 41. In still other embodiments, the implantable port 10 may have hardened material such as stainless steel selectively located along areas such as the upper surface of the port body or the upstream end of the passage 20 which may be frequently engaged by the needle N. The portion of the passage 20 which engages the needle N preferably has a radial stiffness greater than the radial stiffness of the needle.

Although not restricted in this manner, the present invention has particular application with syringes or other pressurized delivery systems for the injection of materials into the body. For example, the present application finds particular use in facilitating the daily injections of insulin required by some patients with diabetes. The present invention may also find application in other drug delivery roles. As shown in FIG. 1, a pressure source such as syringe S is used to deliver fluid into the implantable port 10. The injection pressure from the syringe S is preferably sufficient to open the slit valve 40, thus allowing infusion of drugs or materials into the catheter or conduit 30. It should be understood that the threshold pressure is preferably selected so that a manually operated injection device such as a syringe S can create sufficient pressure to open and flow fluid through the normally closed valve. The threshold level of pressure required to open the slit valve 40 or other pressure sensitive valve element is typically between 0.25 and 25.0 psi, and preferably between about 1.0 and 5.0 psi. A small syringe used for insulin delivery can easily generate pressures of excess of 100 psi.

Figure 4A:
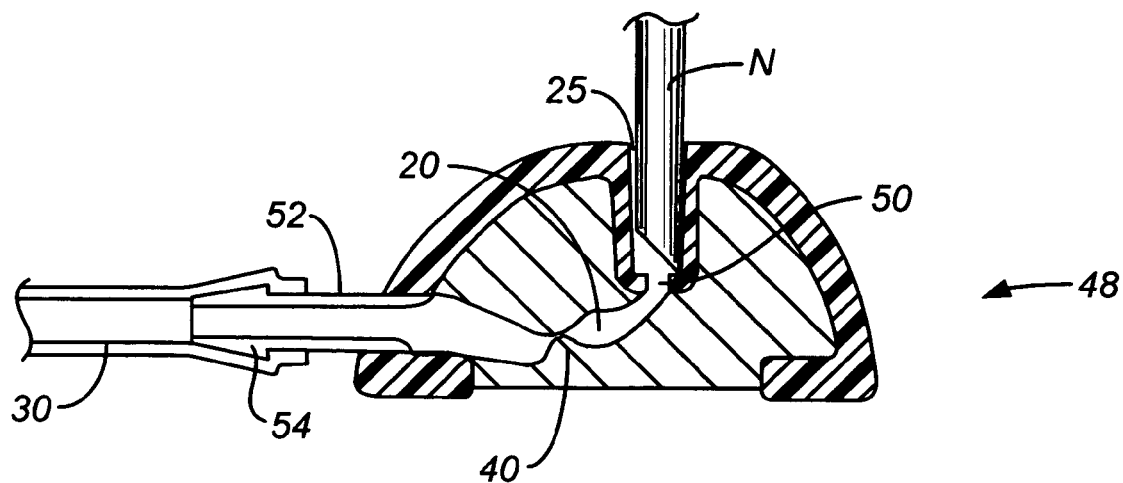
FIGS. 4A–4B show cross-sectional views of alternative embodiments of an implantable port according to the present invention.

Referring now to FIGS. 4A–4B and FIGS. 5A–5D, other embodiments of the access port will be described in further detail. Although the downstream end of the flow passage is preferably disposed at a 90° angle (FIG. 1) relative to the upstream end 22, FIG. 4A shows a port 48 where the upper end 22 of passage 20 may be oriented at other angles as shown by the orientation of flow passage 20. This may allow for other angles of injection as desired. By using an opening 50 of a smaller diameter which prevent further needle penetration, some embodiments of the port may have upstream end 22 axially aligned with the longitudinal axis of the downstream end 24. The smaller diameter or use of some other stop prevents contact or accidental penetration of the pressure-responsive valve element 40 by the needle N. As shown in FIG. 1, however, the opening 50 may be positioned in a variety of orientations, such as on the side wall of upstream portion 22, depending on the configuration of the passage 20. Additionally, the port 48 and other port embodiments may have the catheter 30 coupled to the port through a cannula 52 with a nipple 54, instead of integrated with the port as shown in FIG. 1.

Figure 4B:
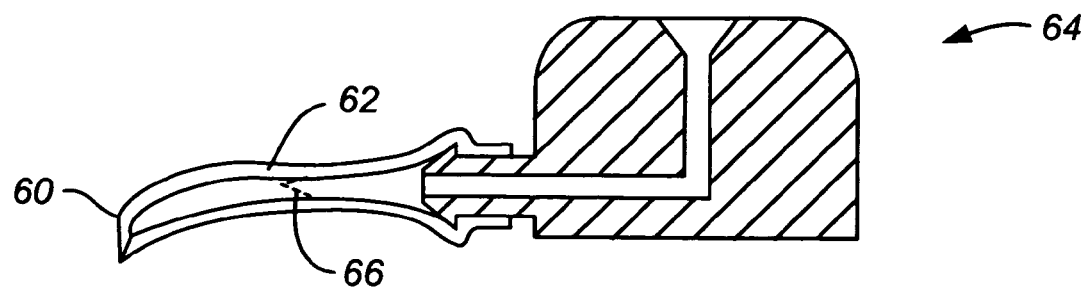

FIG. 4B shows a further embodiment of the port of the present invention where the pressure-activated valve 60 is located at a distal tip of the catheter 62. The fluid flows in a passage that extends from the port through the catheter. The port 64 used in this embodiment typically does not have a valve located within the port. The valve may be located at the distal tip of the catheter or anywhere along the catheter 62. For example, a valve 66 (shown in phantom) may be located at a midpoint of the catheter 62.

Figure 5A:
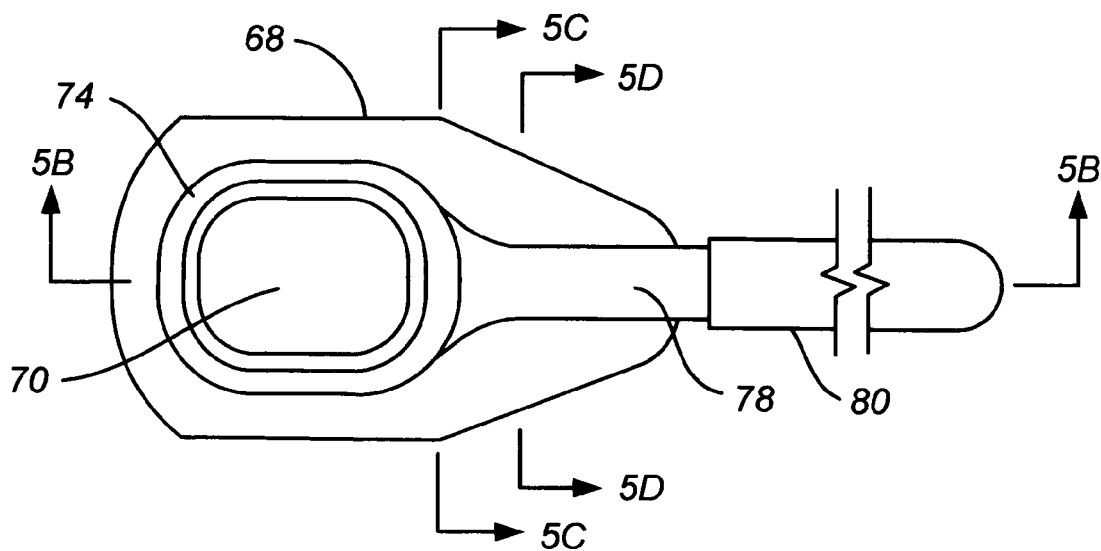
FIGS. 5A–5D show top and cross-sectional views of another embodiment of an implantable port according the present invention.
Figure 5B:
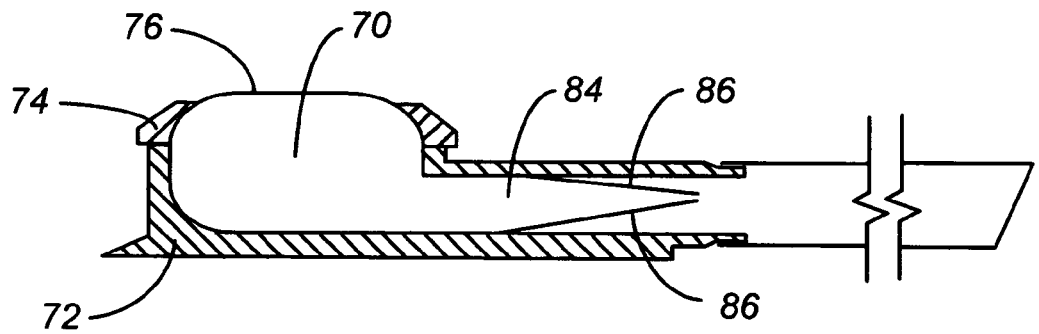
Figure 5C:
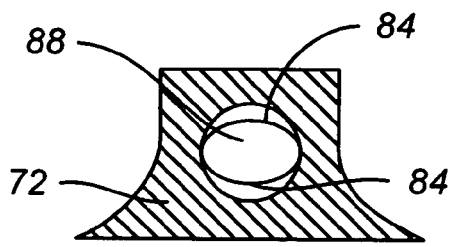
Figure 5D:
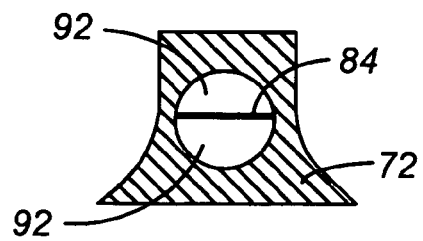

Referring to FIGS. 5A–5D, there is depicted another embodiment of the implantable port of the present invention. As shown in FIG. 5A, this implantable port device 68 employs a single fluid chamber 70. The base and sides of the fluid chamber 70 are formed by the walls of the body 72 of the device 68. As is best seen in FIGS. 5B–5D, the body 72 is shaped so as to define the base and sides of the fluid chamber 70, and is further shaped to accept a cover 74. The cover 74 serves to hold a replaceable diaphragm 76 which forms the top of the fluid chamber 70. The cover 74 and the body 72 are shaped to allow for easy removal of the cover 74 if replacement of the diaphragm 76 is needed. An outlet 78 extends from the fluid chamber 70 and serves to connect the chamber 70 with a cannula 80. The cannula 80 connects the fluid chamber 70 to the target vascular structure, which may be an artery or vein.

As seen in FIG. 5B, a cross section taken along line 5B—5B, the implantable port 68 employs a flap valve device 84 comprised of two sheets of compliant material 86 layered upon each other and bonded to each other along their lateral edges. This configuration allows for creation of an opening 88 between the two sheets of compliant material 86, as shown in FIG. 5C, a cross section taken along line 5C—5C. Opening 88 within the cannula 80 is created when positive pressure is achieved within the fluid chamber 70 or when the flap valve 84 is traversed by a percutaneous needle through the diaphragm 76. Obliteration of the opening 88 and thus closure of the flap valve 84 is achieved by reversal of the pressure gradient attended by removal of the percutaneous needle and exertion of extravascular pressure upon extralumenal portions 92 within the cannula 80, as shown in FIG. 5D, a cross section along line 5D—5D. Additionally, the fluid chamber 70 and connecting cannula 80 may be filled with anticoagulant material or anti-microbial cleaning fluids when the port 68 is not in use. Thus, the pressure flap valve 84 prevents reflux of blood and subsequent washout of anticoagulant material or anti-microbial cleaning fluids during periods when the device 68 is not is use.

The body 72 of the implantable port 68 may be manufactured of surgical metal. Other materials of manufacture are acceptable provided they are compatible with the person or animal into which the port 68 is implanted, and do not adversely affect the tissue to which the port 68 is attached. Additionally, the body 72 should be manufactured of a material of sufficient hardness to resist being damaged or gouged by needles or other tissue penetrating elements which will be inserted through the diaphragm 76 into the fluid chamber 70. The diaphragm 76 should be manufactured of a material tolerant of multiple penetrations with needles without sacrificing the integrity of the diaphragm 76. The cannula 80 may be manufactured of PTFE, or other suitable material which is compatible with the surrounding tissues and is resistant to collapse. The flap valve 84 is preferably manufactured of the same material as the cannula 80, but may be manufactured of any suitable material which has sufficient flexibility to allow passage of fluid through the lumen of the cannula 80 when a pressure differential exists between the target vascular structure and the fluid chamber 70, but will also retard flow or diffuison through the lumen of the cannula 80 when no significant pressure differential exists.

Figure 6:
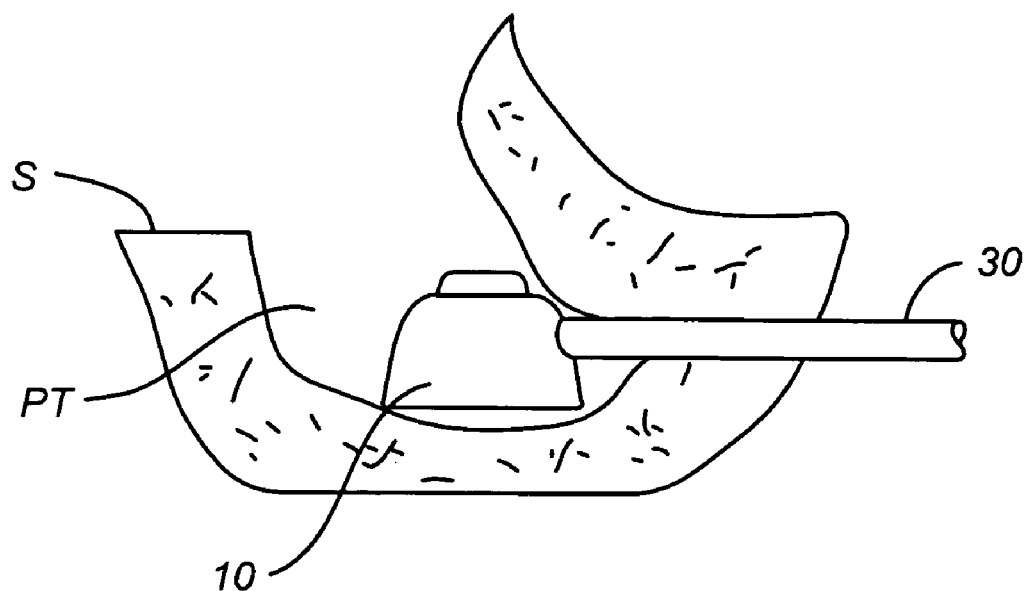
FIGS. 6–7 illustrate one technique for creating and accessing a subcutaneously implanted port according to the methods of the present invention.
Figure 7:
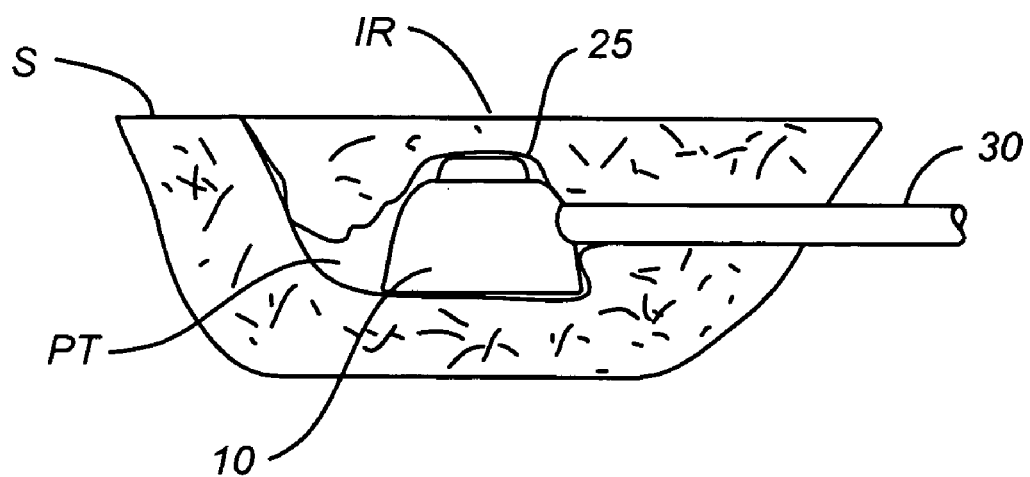
Figure 8:
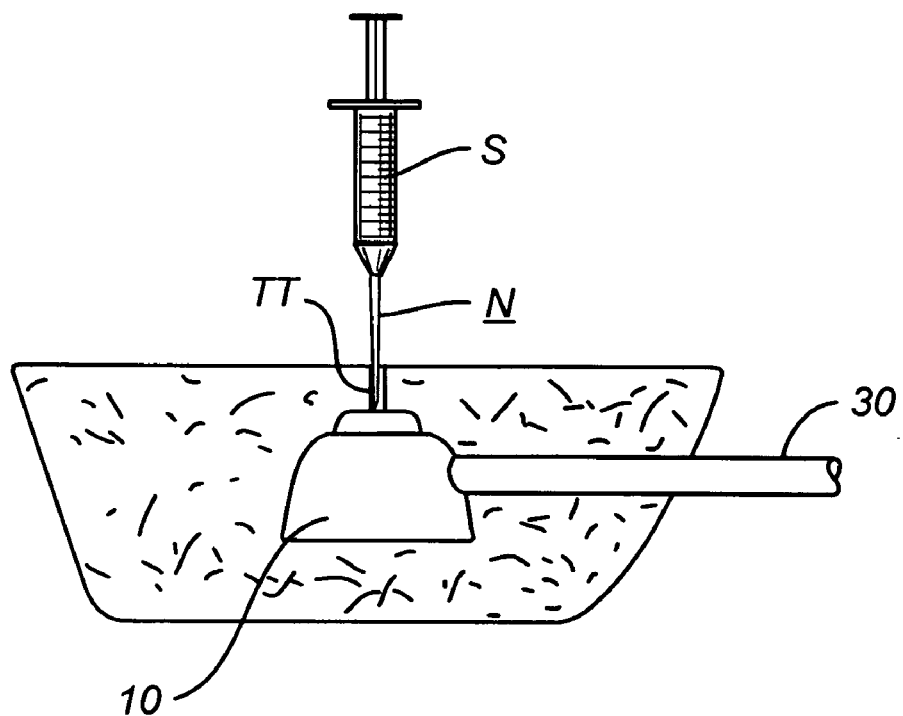
FIGS. 8–9 illustrate use of an access tube for creating and accessing a subcutaneously implanted port according to the methods of the present invention.

Referring now to FIGS. 6–7, a method for implanting the port 10 within the body of the patient will now be described. A port 10 is implanted by creating a tissue pocket PT by making an incision in the skin S and forming the pocket laterally from the incision. The port 10 may then be placed in the pocket PT and connected to a cannula in any manner. A presently preferred manner of connecting the port 10 to the cannula 30 is described in co-pending application Ser. No. 09/238,523 (filed on Jan. 27, 1999, entitled Access System and Methods having Reversible Cannulas), the full disclosure of which is incorporated herein by reference. After the tissue pocket PT is closed, as shown in FIG. 7, an intact region of skin IR will overlay the access tube target aperture 25. A tissue penetrating element, which may be a needle, rod, stylet, tube, or virtually any other penetrating element, may then be introduced through the intact region of skin IR, as shown in FIG. 8. Other suitable tissue penetrating elements are described in co-pending U.S. patent application Ser. No. 09/161,068 (now U.S. Pat. No. 6,120,492), full disclosure of which is incorporated herein by reference for all purposes. The tissue tract of the present invention may be established at any time after a port has been subcutaneously implanted. In many instances, it will be desirable to begin creating the tissue tract at the time the port is initially implanted.

In FIG. 8, a syringe S having a syringe needle N is used as the penetrating IT, element, but it will be appreciated that this is not necessary for initial tissue tract formation. Other access tubes may be used during the initial periods. To help form the tissue tract, the penetrating element may be left in place transcutaneously through the skin for a time sufficient to at least begin forming the tissue tract, usually for at least one week, preferably for at least two weeks. After that initial time, the tissue penetrating element may be removed and the resulting tissue tract accessed using access tubes according to the method of the present invention described below. Continued accessing of the port 10 through the preformed tissue tract will continue to cause scarring and denervation of the tissue tract, further establishing and defining the tissue tract over time. A particular advantage of this method for creating the access tract is that the tract will be formed simultaneously with healing of the surgical introduction of the port and associated subcutaneous cannula. A further advantage, when an access tube is used as the penetrating element, is that fluids may be introduced and removed from the port during the healing period.

Once implanted, the port 10 will have an aperture or opening 25 which is preferably oriented to receive a vertically aligned needle. That is, the access needle N will preferably be percutaneously introduced through the skin surface in a direction which is normal to or perpendicular to the plane of the skin at the point where the needle is being introduced. While vertical access is preferred and may be accomplished using the exemplary ports of the present invention, percutaneous access according to the present invention may also be achieved used non-vertical access direction, i.e. where access is accomplished by penetrating a needle or other device at a relatively low angle relative to the skin, often between 15° and 45° relative to the skin surface. Preferably, the port 10 of the present invention does not have a needle guide channel, trough, or extended funnel at the opening of passage 20 since such a funnel or trough may allow the user to penetrate the access tube through different access tracts.

After entering the port 10, the access needle N will preferably engage with a tapered portion of the upstream end 22 of passage 20 to form a seal. The needle N does not engage the valve element 40, which in the preferred embodiment, is located in a portion of the passage 20 oriented at a 90° to the upstream end 22. The access tube may inserted using a method as further described in commonly assigned, copending application Ser. No. 09/238,461 (entitled Devices and Methods for Accessing an Implanted Port, filed Jan. 29, 1999), the full disclosure of which is incorporated herein by reference. The access tube or needle N is inserted to establish a flow path with a lumen in cannula 30, where the cannula may be connected to a blood vessel or other body lumen or cavity, as described in detail in co-pending application Ser. No. 08/856,641, filed on May 15, 1997, now U.S. Pat. No. 5,931,829. The access needle N may be aligned over the aperture 25 by manually feeling the top of the port 10. The port 10 is generally symmetric with the aperture 25 positioned in the center of the port. The user can feel the periphery of the port P and visually determine its center. The access needle N is then vertically penetrated through the skin and into the aperture, as shown in FIG. 8. The thickness of tissue T overlying the aperture is generally from 3 mm to 15 mm, as described above.

Figure 9:
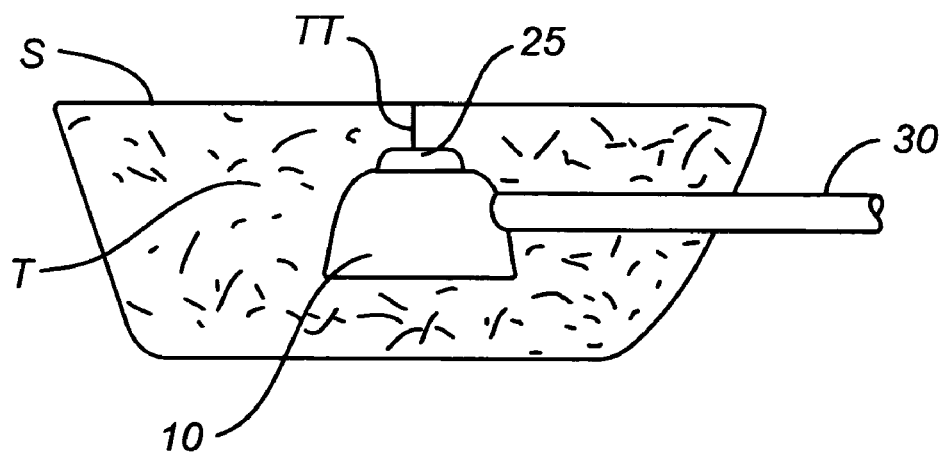

Withdrawal of the needle will leave a tissue tract TT through the tissue T overlying the port 10 (as shown in FIG. 9). Because the internal valve element 40 of port 10 will have closed, fluid from the body lumen such as the peritoneum, a blood vessel, tissue catheter, or other cavities will be inhibited. Both the vertical orientation of needle entry and the valve which inhibits back bleeding or fluid backflow into the tissue tract after withdrawal of the needle, contribute to the lessening or elimination of scab formation and reduction in patient trauma and rapid healing in a non-fibrous manner. Surprisingly, such benefits may be achieved even when using the preferred large bore access needles described above. The rapid healing and minimum trauma have been found even when the port is accessed as many as four times per day or more. Additionally, ports may be irrigated with anti-microbial cleaning fluids when a needle smaller than the needle seal diameter is used.

Figure 9A:
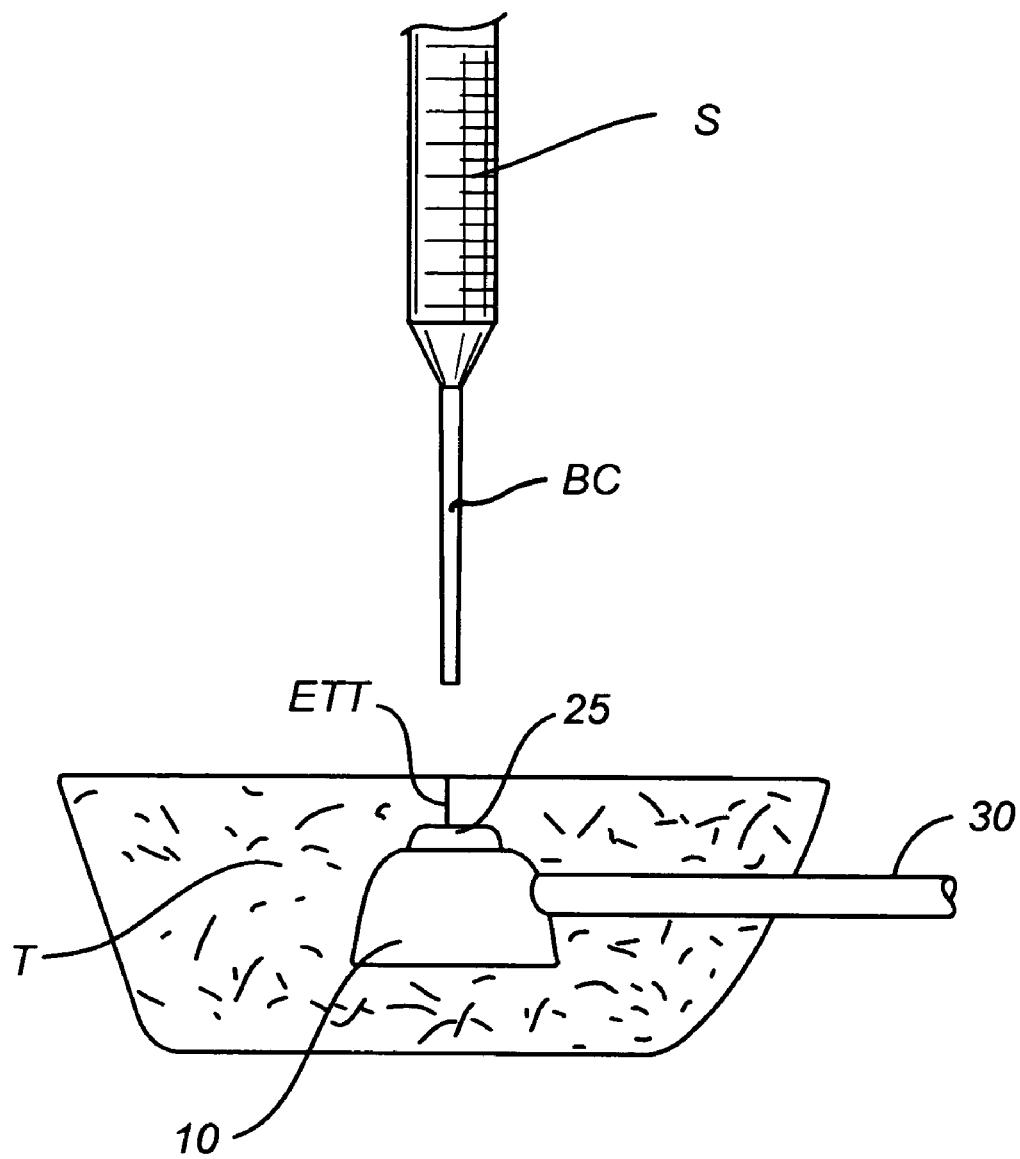
FIG. 9A illustrates use of a blunt cannula for accessing the implanted port through an established tissue tract according to the methods of the present invention.

In some cases, after the access tissue tract is established ETT, it will not be necessary to provide a sharpened element in order to assist in percutaneous introduction, as shown in FIG. 8. That is, a blunt cannula BC may be able to pass inwardly through the established tissue tract ETT, as shown in FIG. 9A. Usually, the blunt cannula will have a diameter which is larger than that of the tissue tract which will have collapsed after the needle was removed in the previously described treatment protocol. Thus, as the blunt cannula is introduced through the established tissue tract, the tissue tract will be dilated.

Figure 10:
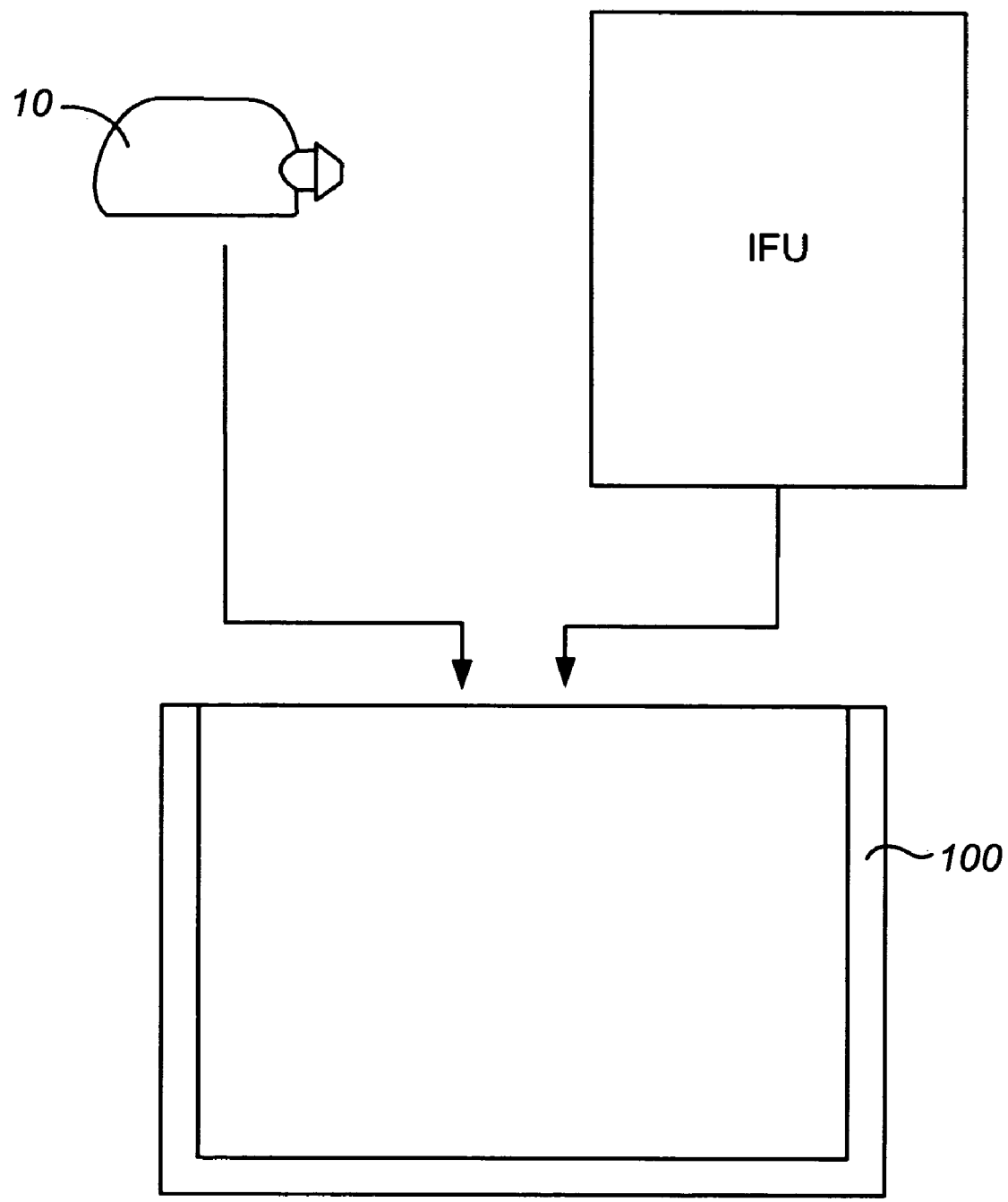
FIG. 10 illustrates a kit according to the present invention comprising a subcutaneously implantable port, a package, and instructions for use describing how to create an access tract according to the present invention.

Referring now to FIG. 10, a port 10 may be packaged together with instructions for use (IFU) in a kit. A conventional package 100, which may be in the form of a pouch, tray, box, tube, or the like, may be used to contain both the port and the instructions for use. Additional kit components, such as a penetrating element, access tube, a catheter, or the like, may also be included in the kit. Optionally, but not necessarily, all kit components may be sterilized within the package, and the instructions for use may be set forth on a separate sheet of paper and/or on the packaging itself. The instructions may set forth any of the aspects of the method of the present invention for implanting the port or subsequently accessing the port using an access tube as described above.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for delivering a substance to a blood vessel, said method comprising:

percutaneously introducing an access tube to an implanted port having a flow passageway with an upstream end, a downstream end, and a valve element in the flow passageway and monolithic with the port, wherein the access tube is introduced to seat in the passage but does not engage the valve element and wherein the flow passage is connected directly to the blood vessel; and introducing said substance into the flow passage through the access tube at a pressure sufficient to open the valve element to permit flow through the flow passageway to the blood vessel.

2. A method as in claim 1 further comprising repeatedly accessing the implanted port with said access tube through the same access tract at intervals and over a time period sufficient to cause scar tissue formation over the access tract.

3. A method as in claim 1 further comprising locating said implanted port by manually aligning the access tube with a line from the skin entry point of an access tract to the aperture on the port.

4. A method as in claim 1 further comprising locating the port by manually feeling the port to determine the position of the aperture.

5. A method as in claim 1, wherein percutaneously introducing further comprises introducing the access tube through a skin layer overlying the implanted port having a thickness in the range from 3 mm to 20 mm.

6. A method as in claim 1, wherein the access tube comprises a blunt cannula.

7. A method as in claim 1, wherein the introducing step comprises orienting the access tube generally vertically with respect to the skin surface.

* * * * *